United States Patent [19]

Kavka

[11] Patent Number: 4,639,520

[45] Date of Patent: Jan. 27, 1987

[54] PREPARATION OF 14-HYDROXY-N-ETHOXY-CARBONYL-NORCODEINONE

[75] Inventor: Frank Kavka, St. Louis, Mo.

[73] Assignee: Mallinckrodt, Inc., St. Louis, Mo.

[21] Appl. No.: 593,752

[22] Filed: Mar. 27, 1984

[51] Int. Cl.$^4$ ........................................... C07D 489/08
[52] U.S. Cl. ...................................... 546/45; 546/44
[58] Field of Search ................................. 546/44, 45

[56] References Cited

U.S. PATENT DOCUMENTS 2,772,270 11/1956 Weiss .................................. 260/285
4,472,253 9/1984 Schwartz .............................. 546/45

FOREIGN PATENT DOCUMENTS 2515184 4/1983 France .
8203204 3/1983 Netherlands .

OTHER PUBLICATIONS

Schwartz & Wallace, "Efficient Synthesis of 14-Hydroxymorphinans from Codeine", *J. Med. Chem.* (1981), 24, pp. 1525–1528.

Hauser et al., "14-Hydroxycodeinone. An Improved Synthesis", *J. Med. Chem.* (1974), vol. 17, No. 10, p. 1117.

Iijima, Rice & Brossi, "The Oxidation of Thebaine with m-Chloroperbenzoic Acid", *Helv. Chim. Acta* (1977), vol. 60, Fasc. 7 Nr. 213, pp. 2135–2137.

Kirk & Wiles, "The Reaction of m-Chloroperbenzoic Acid with 3-Acetoxy-Steroidal 3,5-Dienes," *Chem. Comm.* (1970), p. 518.

Kirk & Wiles, "Competing Reactions in the Peroxyacid Oxidation of 3-Alkoxy-Steroidal 3,5-Dienes," *Chem. Comm.* (1970), pp. 1015–1016.

Bentley, *The Chemistry of the Morphine Alkaloids*, 1954, pp. 251, 252 & 262.

*Primary Examiner*—Donald G. Daus
*Assistant Examiner*—Diana G. Rivers
*Attorney, Agent, or Firm*—R. G. Jackson; L. N. Goodwin; R. J. Klostermann

[57] ABSTRACT

N-ethoxycarbonyl-14-hydroxynorcodeinone is prepared by contacting N-ethoxycarbonyl-norcodeinone enol acetate with an aromatic or aliphatic mono-basic or poly-basic peroxy-acid under reaction conditions effective for substituting an —OH group in the 14-position of the norcodeinone enol acetate.

In a preferred embodiment the reaction conditions include effecting the contacting in the presence of (A) a moderately strong acid having a $pK_a$ of from about 0.3 to about 3.5, (B) an inert organic solvent, and (C) in the substantial absence of water.

Codeine is converted to noroxymorphone by an improved process employing the above method for introducing the 14-hydroxy group into the codeine derivative.

21 Claims, No Drawings

PREPARATION OF 14-HYDROXY-N-ETHOXY-CARBONYL-NOR-CODEINONE

This invention relates to a method for preparing 14-hydroxy-N-ethoxycarbonyl-norcodeinone from N-ethoxycarbonyl-norcodeinone enol acetate and to an improved process for preparing noroxymorphone from codeine 14-hydroxymorphinans, including such "nal" compounds as naloxone, naltrexone, and nalbuphine are important morphine derivatives due to their behavior as potent analgesics and/or narcotic antagonists. Prior to the present invention, among the most practical synthetic routes to the preparation of these pharmaceuticals have been processes which utilize thebaine as a starting material. In accordance with heretofore known processes, thebaine is oxidized to 14-hydroxycodeinone by use of m-chloroperbenzoic acid in an acetic acid/trifluoroacetic acid mixture or by a mixture of hydrogen peroxide and formic acid. 14-hydroxycodeinone is catalytically reduced to oxycodone which in turn is O-demethylated with boron tribromide to yield oxymorphone. After blocking of the hydroxyl groups with suitable blocking agents such as acetyl groups, the oxymorphone derivative is reacted with cyanogen bromide to yield an N-cyanodihydronormorphinone derivative which is thereafter hydrolyzed to 14-hydroxydihydronormorphinone (noroxymorphone), an important intermediate for preparation of naloxone, naltrexone and nalbuphine. However, such thebaine-based syntheses are not entirely satisfactory for a number of reasons. For example, thebaine is in limited supply and its cost is high, thereby contributing to high cost of the noroxymorphone and the 14-hydroxymorphinans derived from it.

Because of the scarcity and high cost of thebaine, efforts have been made in the art to devise methods for the synthesis of noroxymorphone and noroxycodone from compounds in more plentiful supply than thebaine.

Schwartz, Dutch Patent Application Document No. 8203204, published Mar. 16, 1983, and French Patent Application, Document No. 2,515,184, published Apr. 29, 1983, provides such an alternative route to noroxycodone and noroxymorphone and the above "nal" compounds derivable therefrom. In the Schwartz method, oxidation of N-ethoxycarbonylnorcodeinone dienol acetate (derivable from codeine) with singlet oxygen affords 14-hydroxy-N-ethoxycarbonyl-norcodeinone, which is thereafter converted to noroxymorphone via N-ethoxycarbonyl-noroxycodone. In the above Schwartz patent applications, there is disclosed a total synthesis or process for preparing noroxymorphone from codeine wherein (A) codeine is converted to N-ethoxycarbonyl-norcodeine, (B) the N-ethoxycarbonyl-norcodeine is converted to N-ethoxycarbonyl-norcodeinone, (C) the N-ethoxycarbonyl-norcodeinone is converted to N-ethoxycarbonyl-norcodeinone dienol acetate, (D) the dienol acetate is converted to 14-hydroxy-N-ethoxycarbonyl-norcodeinone, (E) the 14-hydroxy-N-ethoxycarbonyl-norcodeinone is converted to N-ethoxycarbonyl-noroxycodone, and (F) noroxymorphone is formed either (i) by converting the N-ethoxycarbonyl-noroxycodone to noroxycodone followed by converting the noroxycodone to noroxymorphone or (ii) by converting the N-ethoxycarbonyl-noroxycodone to N-ethoxycarbonyl-noroxymorphone followed by converting the N-ethoxycarbonyl-noroxymorphone to noroxymorphone, However, there is a substantial need in the art for a lower cost, more efficient method of introducing a 14-β-hydroxy group into N-ethoxycarbonyl-norcodeinone dienol acetate. There is also a substantial need in the art for an improved process for preparing noroxymorphone from codeine.

As indicated above, preparation of 14-hydroxycodeinone via oxidation of thebaine with m-chloroperbenzoic acid or other peroxy compounds has heretofore been known.

Hauser et al., "14-Hydroxycodeinone. An Improved Synthesis", *Journal of Medicinal Chemistry* (1974), Vol 17, no. 10, page 1117, states "14-Hydroxycodeinone . . .

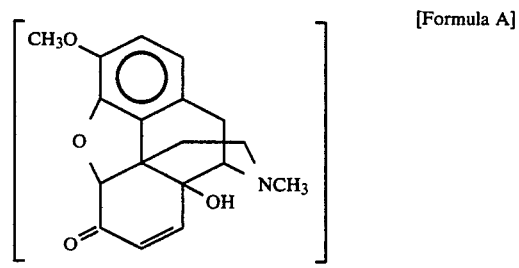

[Formula A]

is normally prepared by oxidation of thebaine

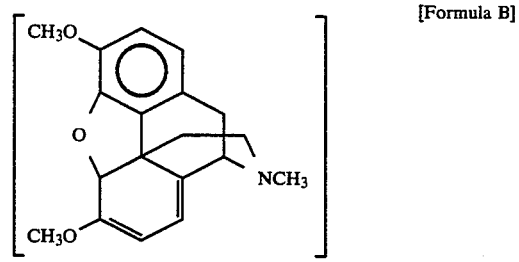

[Formula B]

with either hydrogen peroxide or potassium dichromate in acetic acid", citing M. Freund and E. Speyer, *J. Prakt Chem.*, 94(2), 135(1916). Hauser et al. also discloses synthesis of 14-hydroxycodeinone using an alternate procedure for the thebaine oxidation wherein m-chloroperbenzoic acid ("mClPBA") is added to a stirred solution of thebaine in a mixture of acetic acid and trifluoroacetic acid. The article reports 74% yield of product recrystallized from ethanol containing a small amount of chloroform. The total of the reported times for the various stages of the procedure is 75 minutes from initial m-chloroperbenzoic acid addition through a final stirring of the reaction mixture prior to cooling and pouring into ice water.

Iijima, Rice and Brossi, "The Oxidation of Thebaine with m-Chloroperbenzoic Acid", *Helvetica Chimica Acta* (1974), Vol. 60, Fasc. 7-Nr. 213, pages 2135-37, states "The [above-mentioned] procedure for oxidation of thebaine with . . . [mClPBA] reported by Hauser et al. is in our experience rather sensitive to small changes in the reaction conditions." Iijima et al. continues: "Using shorter reaction times affords, after extraction of the basified solution with chloroform and crystallizaton from ethanol, the unsaturated ketone 2 [14-hydroxycodeinone], however in only 24% yield instead of the reported 74%." The oxidation reaction conditions disclosed in the "Experimental part" of Iijima et al (page 2136) include a total of 35 minutes from initial mClPBA addition through final stirring of the reaction mixture prior to cooling and pouring into ice water.

Introduction of β-hydroxy groups into 3-acetoxy- and 3-alkoxy-steroidal 3,5-dienes via reaction thereof with m-chloroperbenzoic acid has also heretofore been known. However, aqueous dioxan solvent has been deemed necessary to form the steroidal 6β-hydroxy-4-ene-3-ones in good yields from the acetoxy-steroidal 3,5 dienes.

Kirk and Wiles, "The Reaction of m-Chloroperbenzoic Acid with 3-Acetoxy-steroidal 3,5-Dienes," *Chemical Communications* (1970), page 518 ("Kirk$_I$") states that:

"Enol Acetates (cf. I) [Formula C below]

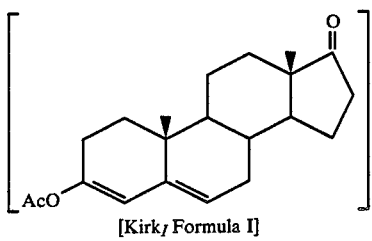

[Formula C]

[Kirk$_I$ Formula I]

or enol ethers of steroidal 4-en-3-ones are reported to give the corresponding 6β-hydroxy-4-en-3-ones (II)

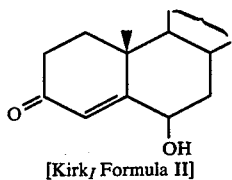

[Formula D]

[Kirk$_I$ Formula II]

on reaction with peroxy-acids [citing J. Romo et al., *J. Org. Chem.* 1954, 19, 1509; J.P.Dusza et al., ibid., 1963, 28, 92]. Yields, however, are generally low, and in our experience, not reproducible under the conditions described." Kirk$_I$ discloses that 3-acetoxyandrosta-3,5-diene-17-one of its formula I (Formula C above) reacts rapidly with mClPBA in solvents of low polarity (benzene, carbon tetrachloride, dichloromethane, etc.), with addition of OH and O.CO.C$_6$H$_4$Cl groups on to the 5,6-double bond of the enol acetate, to form an unstable 1:1 addition compound of the formula

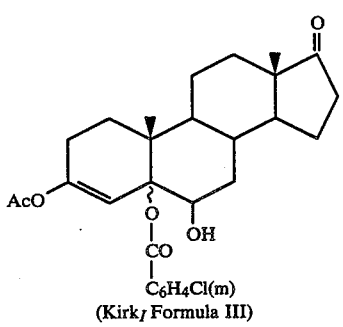

(Formula E)

(Kirk$_I$ Formula III)

with little, if any, production of the 6β-hydroxy-steroid of its formula II (Formula D above).

Kirk$_I$ further discloses that "other steroidal 3-acetoxy-3,5-dienes (e.g., the enol acetate of cholest4en-3-one) gave similar addition products with [mClPBA] . . . ;" in the absence of a 17-oxo group, 6β-hydroxy-4-en-3-ones were obtained in low and erratic yields; "However, the latter compounds were formed in good yields (up to 90%) if the reaction of any of these enol acetates with peroxy-acid was carried out in aqueous dioxan."

In a subsequent Kirk and Wiles article, "Competing Reactions in the Peroxyacid Oxidation of 3-Alkoxy-steroidal 3,5-Dienes," *Chemical Communications* (1970), pages 1015–1016 ("Kirk$_{II}$"), there is disclosed reaction between some dienol ethers of the formula

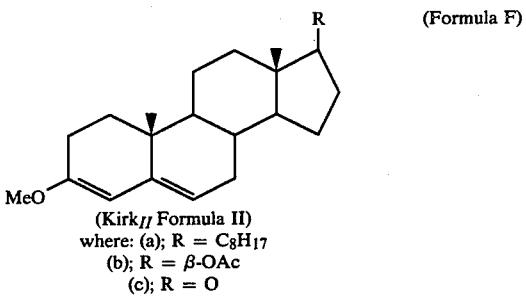

(Formula F)

(Kirk$_{II}$ Formula II)
where: (a); R = C$_8$H$_{17}$
(b); R = β-OAc
(c); R = O and peroxy-acid, using mClPBA. Kirk$_{II}$ discloses that in either the cholestane series, Formula F (a), or androstane series, Formula F (b) or (c) the "major products were the 3,4-seco-aldehyde-ester" of the formula

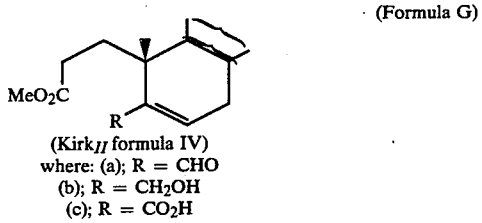

(Formula G)

(Kirk$_{II}$ formula IV)
where: (a); R = CHO
(b); R = CH$_2$OH
(c); R = CO$_2$H

"or the 6β-hydroxy-4-en-3-one" of the formula

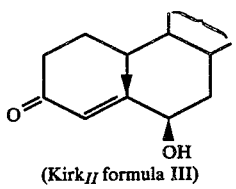

(Formula H)

(Kirk$_{II}$ formula III)

Kirk$_{II}$ adds: "Their proportions depended both upon the solvent and upon the method of mixing the reactants."; and "Anhydrous solutions (dioxan, carbon tetrachloride, dichloromethane, etc.) and immediate addition of an excess of peroxy-acid favour the aldehyde ester [Formula G (Kirk$_{II}$ Formula IVa) above] . . . , whereas aqueous organic solvents, and gradual addition of peroxy-acid to the steroid, favour the 6β-hydroxy compound [Formula H (Kirk$_{II}$ formula III) above]."

Kirk$_{II}$ further discloses (at p. 1016) that the dienol ether (Formula F, Kirk$_{II}$ formula II, above) is oxidized preferentially at the 3,4-bond in the absence of water, but at C-6 when water is present; that such behavior is "almost unique among the known reactions of 3,5-dienol ethers (and esters), which are normally attacked at C-6 by electrophilic reagents. [citing R. Gardi et al., *J. Org. Chem.*, 1967, 32, 2647 at 'ethers' and D. N. Kirk et al., 'Steroid Reaction Mechanisms,' Elsevier, Amsterdam, 1968, p 184 at 'esters'.]"

It has surprisingly now been found that 14-hydroxy-N-ethoxycarbonyl norcodeinone can be repeatedly formed in high yields at fast rates and with good reliability by contacting N-ethoxycarbonyl-norcodeinone enol acetate with peroxy-acid compounds in the substantial absence of water. The present invention substantially fulfills the above-mentioned need for a lower cost, more efficient method of introducing a 14β-hydroxy group into N-substituted norcodeinone dienol acetate. This invention also substantially fulfills the above-mentioned need for an improved process for preparing noroxymorphone from codeine.

DESCRIPTION OF THE INVENTION

Generally stated, the present invention provides a method for preparing N-ethoxycarbonyl-14-β-hydroxynorcodeinone, which comprises contacting N-ethoxycarbonylnorcodeinone enol acetate (i) with (an aromatic or aliphatic) (mono-basic or poly-basic) peroxy-acid (ii) under Reaction Conditions effective for substituting an —OH group in the 14-position of norcodeinone enol acetate.

In a preferred embodiment, the Reaction Conditions include the effecting said contacting (1) in the presence of (A) a moderately strong acid having a $pK_a$ of from about 0.3 to about 3.5

(B) an inert organic solvent which is a solvent for and sustantially non-reactive with the N-ethoxycarbonyl-norcodeinone enol acetate, said peroxy-acid and said moderately strong acid; said solvent being present in a solubilizing amount for each of the N-ethoxycarbonyl-norcodeinone enol acetate, said peroxy-acid and said moderately strong acid, (2) in the substantial absence of water, and (3) with at least about 1 gram-equivalent of said peroxy-acid being present per gram-mole of the N-ethoxycarbonyl-norcodeinone enol acetate.

This invention also provides an improvement in codeine-to-noroxymorphone total-synthesis processes of the type described in the above-mentioned, published Schwartz patent applications. The improvement comprises employing the above method of this invention as step D of such total synthesis of noroxymorphone from codeine.

DETAILED DESCRIPTION OF THE INVENTION AND OF THE MANNER AND PROCESS OF MAKING AND USING IT

In the method of the present invention N-ethoxycarbonyl-14-βhydroxynorcodeinone (Formula I below)

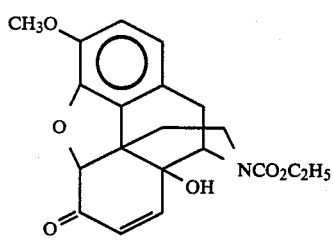
(Formula I)

is prepared by reactively contacting N-ethoxycarbonyl-norcodeinone enol acetate (Formula J below)

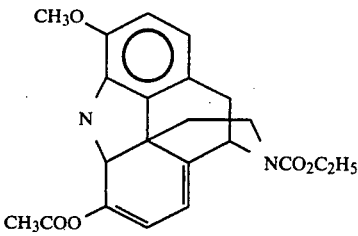
(Formula J)

with a peroxy oxidation agent capable of introducing a β-oriented —OH group in the 14- position of the dienol acetate. Such peroxy oxidation agent may be, for example, an aromatic or aliphatic, mono-basic or poly-basic carboxylic peroxy-acid. Suitable peroxy-acids include, for example, chloroperbenzoic acid (preferably m-chloroperbenzoic acid), peracetic acid, perbenzoic acid, perphthalic acid, nitroperbenzoic acid (preferably p-nitroperbenzoic acid), performic acid and permaleic acid. The peroxy-acid is preferably chloroperbenzoic acid and more preferably is m-chloroperbenzoic acid.

The peroxy-acid may be formed in situ, that is, in the presence of the dienol acetate, by reaction of hydrogen peroxide with the corresponding acid. Preferably, however, contacting of the dienol acetate is effected with peroxide-acid prepared outside the presence thereof.

The act of reactively contacting the norcodeinone dienol acetate of Formula J with the peroxy oxidation agent is effected under Reaction Conditions effective for introducing or substituting an —OH group in the 14-position of the dienol acetate such that N-ethoxycarbonyl-14-hydroxynorcodeinone of Formula I is parepared.

Preferably, the peroxy oxidation agent, sometimes referred to herein simply as the peroxy-acid or per-acid, is added to a solution or other mixture containing the dienol-acetate in an inert organic solvent. That is, the organic solvent is a solvent for and substantially non-reactive with the N-ethoxycarbonyl-norcodeinone enol acetate and the per-acid. The solvent advantageously is present in a solubilizing amount for each of the N-ethoxycarbonyl-norcodeinone acetate and the per-acid.

The organic solvent is preferably a polar organic solvent. Suitable classes of solvents include carboxylic acids, aprotic polar solvents, chlorinated hydrocarbons, carboxylic acid nitriles, carboxylic acid esters, ethers, mixtures thereof and the like. Carboxylic acids, aprotic polar solvents, chlorinated hydrocarbons and mixtures thereof are generally preferred. Suitable solvents include, for example, acetic acid, dimethylformamide, chloroform, methylene chloride (dichloromethane), acetonitrile, 1,2-dimethoxymethane, propyl acetate and mixtures thereof. Acetic acid is preferred, while glacial acetic acid is most preferred.

In addition to the solvent and the dienol acetate, the reaction mixture may include other components. For example, the reaction mixture may include agents effective for inhibiting formation of 7,8-epoxide derivatives of the dienol acetate and other side reaction products. Although the compound of Formula I can be obtained where high-strength acids having $pK_a$ of less than 0.3 (e.g., trifluoroacetic acid) are included in the reaction mixture, such high-strength acids are preferably at least substantially absent therefrom. Surprisingly, as shown in the examples below, absence of trifluoroacetic acid permits higher yield of the desired compound.

The reaction mixture preferably further includes a moderately strong acid having a $pK_a$ of from about 0.3 to about 3.5. It has surprisingly been found that inclusion of such moderately strong acid permits preparation of the 14-hydroxy compound of Formula I in higher yield. Suitable moderately strong acids include, for example, oxalic acid, trichloroacetic acid, phosphoric acid, chloroacetic acid, maleic acid and mixtures thereof. Oxalic acid is preferred.

The reaction conditions preferably further include effecting the contacting of the dienol acetate with the per-acid in the substantial absence of water, i.e., with water not present in an amount greater than 5 percent by weight based on the weight of the reaction mixture. Water is preferably not present in an amount more than 2 percent, and more preferably not present in an amount more than 0.5 percent, on the same basis. Anhydrous reaction conditions are most preferred. Such non-aqueous or anhydrous conditions result in higher yields than are generally attainable under aqueous conditions. Anhydrous reaction conditions may conveniently be provided by employing anhydrous components for the reaction mixture and conducting the reaction under an inert anhydrous atmosphere, e.g., dry nitrogen. Preferably, substantially no water of hydration is present in any of the components of the reaction mixture. Thus, for example, oxalic acid dihydrate may be converted to anhydrous oxalic acid by heating the dihydrate four hours at 100°-110°, followed by cooling in the presence of a dessicant in a dessicator or other air-tight container. Similarly, commercially available peracetic acid (usually containing 10-15% water) advantageously is dried, as by drying with $Na_2SO_4$ (e.g., 20 g per 100 ml) for several hours, decanting and drying at least 16 hours with 4A molecular sieves (e.g., 20 g per 100 ml). The per-acid is preferably added as a solid. Normally liquid per-acids (e.g., peracetic acid and performic acid) are preferably added as solutions thereof in an inert polar solvent, which may be, for example, methylene chloride or the parent or corresponding acid (i.e., acetic acid and formic acid for peracetic acid and performic acid, respectively).

The per-acid is preferably added incrementally to the dienol acetate reaction mixture. The addition may advantageously be made in discrete portions, and at an average rate of from about 0.01 to about 0.1 gram-equivalents per minute per mole of the dienol acetate. Desirably, a total of at least 1 gram-equivalent of the per-acid is added per mole of the dienol acetate. The addition may advantageously be made over a period from about 30 to about 120 minutes, preferably with stirring of the reaction mixture.

The reaction may be conducted at any suitable temperature, e.g., from about 10° C. to about 100° C., preferably about 15° C. to about 25° C. The peroxy-acid may be added in a total amount of, for example, from about 1 to about 2.5 moles per mole of the dienol acetate (pure basis), preferably from about 1.1 to about 1.3 moles per mole on the same basis. The amount of peroxy-acid is preferably increased where the crude dienol acetate starting material is of low assay. For example, about 1.5-1.6 moles and about 2.5-2.6 of m-chloroperbenzoic acid were required for maximum yield from crude dienol acetates of 80% and 43% assay, respectively. Moderately strong acid may be employed in an amount of, for example, from about 0.01 to about 0.5 mole per mole of the dienol acetate. The solvent may be present in an amount of, for example, from about 0.5 to about 10 liters per mole of the dienol acetate.

Where a moderately strong acid is included in the reaction mixture, the solvent preferably is a solvent for, and substantially non-reactive with the moderately strong acid and present in a solubilizing amount therefor.

At the completion of the reaction, the 14-hydroxy compound of Formula I can conveniently be recovered. Recovery can be effected readily by quenching the reaction mixture with water or an aqueous solution of a base (e.g., aqueous $NH_4OH$). Thereafter, the 14-hydroxy compound can be separated by filtration of the quenched mixture, followed by extraction of the filtrate with a water-immiscible solvent (e.g., chloroform), evaporation of the extraction solvent and drying of the resulting solid.

EXAMPLES

Practice of the present invention is illustrated by the following examples. All parts and percentages given throughout this disclosure are by weight unless otherwise indicated.

EXAMPLE 1

This example illustrates preparation of 14-hydroxy-N-ethoxycarbonyl-norcodeinone from N-ethoxycarbonyl-norcodeinone enol acetate employing m-chloroperbenzoic acid and a mixture of acetic acid and trifluoroacetic acid To a stirred solution of N-ethoxycarbonylnorcodeinone dienol acetate (1.00 g) in glacial acetic acid (10 ml), cooled to 17° C. under nitrogen, was added 283 mg m-chloroperbenzoic acid followed by 0.15 g. trifluoroacetic acid. The mixture was stirred at 13°-17° for 1 hour. Additional m-chloroperbenzoic acid (370 mg. total) was added in 4 portions with stirring over 2¼ hours at 12°-18° C. The mixture was heated to 40°-45° C. for 30 minutes, cooled down, and poured into a mixture of 20 g. ice, 5 ml $H_2O$, 14 ml concentrated ammonia, and 25 ml chloroform with stirring. The layers were separated and the aqueous phase was extracted twice with 15 ml chloroform. The combined chloroform layers were washed with 20 ml water. A reverse phase liquid chromatographic assay showed 665 mg. 14-hydroxy-N-ethoxycarbonyl-norcodeinone, which corresponds to 71% yield based on the amount of the enol acetate starting material.

EXAMPLE 2

Example 1 was repeated except that the trifluoroacetic was omitted. Recrystallized 14-hydroxy-N-ethoxycarbonyl-norcodeinone was obtained in 78% yield.

EXAMPLE 3

This Example is illustrative of a preferred embodiment of the present invention.

Crude N-ethoxycarbonyl-norcodeinone enol acetate, approximately 79% to 81% purity and containing 55.6 grams (g.) pure compound, was dissolved in 230 ml glacial acetic acid, $pK_a = 4.76$, under nitrogen in a reaction flask. The resulting solution was cooled to 18° C. and substantially anhydrous oxalic acid (4.1 g.; less than 1% water) was thereafter added with stirring. Next, continued stirring of the contents of the flask and while maintaining the temperature thereof at about 15°-20° C., m-chloroperbenzoic acid (mClPBA) was added incrementally in about 5-10 portions decreasing in weight from about 5½ to about 1½ g. until a total of about 41 g. had been added. Each portion of mClPBA was added over a period of not more than about one minute, with the start of the several additions spaced approximately 10 minutes apart. Approximately 10 minutes after the start of the final mClPBA addition, i.e., approximately 40–120 minutes after the start of the initial mClPBA addition, the reaction mixture was poured into a mixture of 100 ml 50% NaOH, 400 ml NH$_4$OH, and 400 g. ice with stirring and the product was extracted with chloroform repeatedly. The combined chloroform extracts were concentrated to give a residue identified by reverse phase liquid chromatography (RFLC) as 14-hydroxy-N-ethoxycarbonyl-norcodeinone. (Assay: 48.2 g. which corresponds to 93% yield based on the amount of the enol acetate starting material.)

N-ethoxycarbonyl-14-hydroxynorcodeinone is a useful intermediate which may be converted to noroxymorphone as described in the above-cited Schwartz applications. As described therein, this intermediate can be catalytically hydrogenated to N-ethoxycarbonyl-noroxycodone, followed by either (a) acid hydrolysis thereof to noroxycodone and 3-0-demethylation thereof by reaction with a Lewis acid such as boron tribromide to yield noroxymorphone or (b) such 3-0-demethylation followed by acid hydrolysis of the resulting intermediate to yield noroxymorphone.

Noroxymorphone can be converted to antagonists for narcotics and other therapeutically useful products such as naloxone, naltrexone and nalbuphine. See U.S. Pat. Nos. 3,254,088 (naloxone); 3,332,950 (naltrexone); and 3,393,197 (nalbuphine).

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A method for preparing N-ethoxycarbonyl-14-β-hydroxynorcodeinone, which comprises contacting N-ethoxycarbonyl-norcodeinone enol acetate
   (i) with an aromatic or aliphatic non-basic or polybasic peroxy-acid
   (ii) under reaction conditions effective for substituting an —OH group in the 14-position of the norcodeinone enol acetate,
   said reaction conditions including:
   (I) substantial absence of systems for chemical generation of singlet oxygen;
   (II) the presence of
      (A) a moderately strong acid having a pk$_a$ of from about 0.3 to about 3.5 and
      (B) an inert organic solvent which is a solvent for and substantially non-reactive with the N-ethoxycarbonyl-norcodeinone enol acetate, said peroxy-acid and said moderately strong acid; said solvent being present in a solubilizing amount for each of the N-ethoxycarbonyl-norcodeinone enol acetate, said peroxy-acid and said moderately strong acid;
   (III) the substantial absence of water;
   (IV) at least about 1 gram-equivalent of said peroxy-acid being present per gram-mole of the N-ethoxycarbonyl-norcodeinone enol acetate; and
   (V) the substantial absence of an acid having a pK$_a$ of less than 0.3.

2. The method of claim 1 wherein the peroxy-acid is added incrementally to said enol acetate.

3. The method of claim 1 wherein water is not present in an amount greater than 2 percent by weight based on the amount of the reaction mixture.

4. The method of claim 1 wherein said peroxy-acid is selected from the group consisting of chloroperbenzoic acid, peracetic acid, perbensoic acid, perphthalic acid, nitroperbenzoic acid, permaleic acid and performic acid.

5. The method of claim 4 wherein said chloroperbenzoic acid is m-chloroperbenzoic acid and said nitroperbenzoic acid is p-nitroperbenzoic acid.

6. The method of claim 1 wherein said moderately strong acid is selected from the group consisting of oxalic acid, trichloroacetic acid, phosphoric acid, chloroacetic acid and maleic acid.

7. The method of claim 1 wherein said peroxy-acid is chloroperbenzoic acid.

8. The method of claim 1 wherein said peroxy-acid is m-chloroperbenzoic acid.

9. The method of claim 2 wherein said moderately strong acid is oxalic acid.

10. The method of claim 1 wherein said solvent is a polar solvent.

11. The method of claim 10 wherein said polar solvent is selected from the group consisting of carboxylic acids, aprotic polar solvents, chlorinated hydrocarbons, carboxylic acid nitriles, carboxylic acid esters, and ethers.

12. The method of claim 11 wherein said polar solvent is selected from the group consisting of carboxylic acids, aprotic polar solvents and chlorinated hydrocarbons.

13. The method of claim 11 wherein said solvent is selected from the group consisting of dimethylformamide, chloroform, methylene chloride (dichloromethane), acetonitrile, 1,2-dimethoxymethane and propyl acetate.

14. The method of claim 11 wherein said solvent is acetic acid.

15. The method of claim 14 wherein the acetic acid is glacial acetic acid.

16. The method of claim 2 wherein said peroxy-acid is added in portions at an average rate of from about 0.01 to about 0.1 gram-equivalents per minute per mole of said enol acetate.

17. The method of claim 16 wherein a total of at least 1 gram-equivalent of said peroxy-acid is added in discrete portions per mole of said enol acetate during a period of from about 30 to about 120 minutes with stirring of the reaction mixture.

18. The method of claim 1 wherein said reaction conditions further include a reaction temperature of from about 10° C. to about 100° C. incremental addition of said peroxy-acid to said enol acetate in a total amount of from about 1 to about 2.5 moles of peroxy-acid per mole of said enol acetate, presence of from about 0.01 to about 0.5 mole of said moderately strong acid per mole of said enol acetate and presence of from about 0.5 to about 10 liters of said solvent per mole of said enol acetate.

19. In a process for preparing noroxymorphone from codeine wherein (A) codeine is converted to N-ethoxycarbonyl-norcodeine, (B) the N-ethoxycarbonyl-norcodeine is converted to N-ethoxycarbonyl-norcodeinone, (C) the N-ethoxycarbonyl-norcodeinone is converted to N-ethoxycarbonyl-norcodeinone dienol acetate, (D) the dienol acetate is converted to 14-hydroxy-N-ethoxycarbonyl-norcodeinone, (E) the 14-hydroxy-N-ethoxycarbonyl -norcodeinone is converted to N-ethoxycarbonyl-noroxycodone, and (F) noroxymorphone is formed either (i) by converting the N-ethoxycarbonyl-noroxycodone to noroxycodone followed by converting the noroxycodone to noroxymorphone or (ii) by converting the N-ethoxycarbonyl-noroxycodone to N-ethoxycarbonyl-noroxymorphone followed by converting the N-ethoxycarbonyl-noroxymorphone to noroxymorphone, the improvement wherein step (D) comprises:

contacting N-ethoxycarbonyl-norcodeinone enol acetate
 (i) with an aromatic or aliphatic mono-basic or polybasic peroxy-acid
 (ii) under reaction conditions effective for substituting an —OH group in the 14-position of the norcodeinone enol acetate, said reactions conditions including:
 (I) substantial absence of systems for chemical generation of singlet oxygen;
 (II) the presence of
  (A) a moderately strong acid having a p$K_a$ of from about 0.3 to about 3.5 and
  (B) an inert organic solvent which is a solvent for and substantially non-reactive with the N-ethoxycarbonyl-norcodeinone enol acetate, said peroxy-acid and said moderately strong acid; said solvent being present in a solubilizing amount for each of the N-ethoxycarbonyl-norcodeinone enol acetate, said peroxy-acid and said moderately strong acid;
 (III) the substantial absence of water;
 (IV) at least about 1 gram-equivalent of said peroxyacid being present per gram-mole of the N-ethoxycarbonyl-norcodeinone enol acetate; and
 (V) the substantial absence of an acid having a p$K_a$ of less than 0.3.

20. The process of claim 19 wherein said solvent is a polar organic solvent.

21. The process of claim 18 wherein said temperature is from about 15° to about 25° C.

* * * * *